United States Patent
Carlos et al.

[11] Patent Number: 5,849,002
[45] Date of Patent: Dec. 15, 1998

[54] DISPOSABLE DIAPER WITH RECEPTION, DISTRIBUTION-STORAGE AND ANTI-LEAKAGE ZONES WITHIN THE ABSORBENT CORE

[75] Inventors: Alberto Corona Carlos; Carlos Canales Espinosa de los Monteros; Lucia Sanchez Fernandez, all of Puebla, Mexico

[73] Assignee: Productos Internacionales Mabe, S.A, Puebla, Mexico

[21] Appl. No.: 497,058

[22] Filed: Jun. 30, 1995

[30] Foreign Application Priority Data

Jun. 30, 1994 [MX] Mexico ...................................... 945015

[51] Int. Cl.$^6$ ...................................................... A61F 13/15
[52] U.S. Cl. ........................ 604/378; 604/368; 604/385.1
[58] Field of Search ..................................... 604/358, 368, 604/372, 378, 379, 380, 384, 385.1

[56] References Cited

U.S. PATENT DOCUMENTS

| | | |
|---|---|---|
| 3,017,304 | 1/1962 | Burgeni . |
| 4,027,672 | 6/1977 | Karami . |
| 4,213,459 | 7/1980 | Sigl et al. . |
| 4,333,463 | 6/1982 | Holtman . |
| 4,685,909 | 8/1987 | Berg et al. . |
| 4,685,915 | 8/1987 | Hasse et al. . |
| 5,087,506 | 2/1992 | Palumbo . |
| 5,192,606 | 3/1993 | Proxmire et al. . |
| 5,246,431 | 9/1993 | Minetola et al. . |
| 5,514,104 | 5/1996 | Cole et al. . |
| 5,582,603 | 12/1996 | Difilippantonio et al. . |

FOREIGN PATENT DOCUMENTS

| | | |
|---|---|---|
| 0254476 | 1/1988 | European Pat. Off. . |
| 171485 | 10/1993 | Mexico . |

*Primary Examiner*—Robert A. Clarke
*Attorney, Agent, or Firm*—Fish & Richardson P.C.

[57] ABSTRACT

A disposable diaper is described in which the absorbent core's material is distributed in such a way that three zones are made inside of it" one of liquid reception, a zone of distribution-storage, and finally an anti-leakage zone. The reception zone is placed where generally the user discharges urine while using the diaper. This zone is less dense and has a lower specific gravity than the distribution-storage zone that fully surrounds it, in such way that when liquid flows in the reception zone it is immediately absorbed and flows towards the distribution-storage zone, which will distribute the liquid to every zone of the diaper and there it will remain until the diaper is disposed, since when liquid reaches the anti-leakage zone fluid flow is drastically stopped because this zone has lower density than the distribution-storage zone and the liquid will not flow towards it due to the increased size of the capillary radius. This anti-leakage zone surrounds all the distribution-storage zone, shaping all the periphery of the absorbent core, so that as is does not permit liquid flow towards it, it will remain dry and it will completely avoid leakage in any of the zones of the diaper.

18 Claims, 2 Drawing Sheets

DISPOSABLE DIAPER WITH RECEPTION, DISTRIBUTION-STORAGE AND ANTI-LEAKAGE ZONES WITHIN THE ABSORBENT CORE

BACKGROUND OF THE INVENTION

Improvements to disposable diapers are constantly looked for so to make them more comfortable for the user as well as safer, avoiding leakage as much as possible.

At laboratory level as well as in surveys directed to the user's mothers, it has been noticed that the absorbent core in diapers is not used fully, that is, liquid remains only in one part of the core (generally in front) and is not distributed to the other zones of it (the back almost always remains dry). If the user urinates again on the same diaper, the already wet zone will receive urine without distributing it, causing diverse inconvenient phenomena: the user feels uncomfortable being wet, the absorbent core breaks because of the excess weight, and probably there will be leakage because of lack of absorbent capacity.

To employ advantageously the capacity of the absorbent core and to make it work more efficiently many attempts have been made; for example, in U.S. Pat. No. 4,027,672, to Hamzel et al., and assigned to Colgate Palmolive, it is suggested to put more dense channels joined to less dense channels so that the more dense channels distribute liquid rapidly to all the core and the less dense channels serve as storage sites. However, this arrangement presents two problems: first, the fluid flow from a high density zone to a low density zone is hindered or nullified, and second, that in case this flow happens, the low density zone has less capacity to retain the liquids.

In U.S. Pat. No. 4,213,459, to Wayne C. Sigl et al., and assigned to Kimberly-Clark Corporation, it is suggested to place in the back of the diaper, which generally is not used, the high density zone, so that when liquid reaches it, it is distributed internally in this zone. This design has the disadvantage that being the low density zone too big (all of the front part of the diaper), the fluid will distribute slowly and not being trapped quickly, the return of liquids to the surface is favored, producing humidity in the user's skin.

The European Pat. No. 0,254,476, to Alemany et al., and assigned to The Procter & Gamble Company, considers a reception zone located where generally urine is deposited when the user uses the diaper, surrounded by a storage zone; however in this patent the different anatomy of boys and girls is not considered in the reception zone. On the other hand, only reception and storage zones are mentioned and an anti-leakage zone in the whole periphery of the core is not contemplated.

The Mexican Pat. No. 171,485, granted to the assignee hereof, describes a diaper with three different zones in the absorbent core, one of reception, one of distribution and another of storage; the first being of lower density than the distribution zone, surrounding it wholly, and the storage zone of lower density than the distribution zone, which also surrounds it. Although different functions for each of the mentioned zones are considered, in the present invention it is proposed to improve the state of the art, particularly identified by the above-mentioned Mexican patent, giving more efficiency to the use of the absorbent core, and permitting to take advantage of a larger area of the diaper.

Another approach to solve the problem of leakage has been to use adjustment members placed over the topsheet of the diaper; although the acceptance that these adjustment members have had in the market, and the fact that they have helped to reduce the lateral leakage, the more known designs of them seem to have reached the peak of their efficiency, which makes necessary to approach the problem of leakage by way of improvement of the diaper's other structures, as it is in this invention by means of an anti-leakage zone, among other elements, in the absorbent core.

The present invention proposes the use of an absorbent core with a reception zone located where the user deposits the urine when he uses the diaper. This reception zone has the shape of a flask with a long neck so that it includes the zone used by boys (the body of the flask) and the zone used by girls (part of the body of the flask and the neck of it). This reception zone, when the liquid is received by it, absorbs it rapidly and starts distributing in all directions. Surrounding all the reception zone, the distribution-storage zone is located, which distributes the urine toward all the areas of this zone, where it will remain strongly bundled; this zone comprises both the front and the back parts of the diaper. Surrounding all the distribution-storage zone is the anti-leakage zone which, since it has lower density than the distribution-storage zone, makes difficult or stops the liquid flow towards it, preventing it from reaching the edge of the core.

On the other hand, the superabsorbent material inside the absorbent core must be fully mixed with the absorbent material to avoid the blocking and increase the distribution.

What is looked for with this invention is that the absorbent core works more efficiently, that the liquid be properly distributed and that it does not reach the edge of the core to avoid leakage.

To achieve this objective, the weights and the densities of the absorbent material of the core are varied. As an aid to accomplish this main objective, the absorbent material of the core is mixed with the superabsorbent material in a very particular way, which will be explained later.

Thus, the objectives of the present invention are the following:

A) That the absorbent core of a diaper works at its maximum efficiency.
B) That the user is comfortable, feeling dry at any time.
C) To prevent leakage.
D) To lower costs using the necessary amount of superabsorbent material so that it works without blocking the distribution of liquids.

All the foregoing will be explained in detail, and because of this it will be understood much better, with reference to the following description of a presently preferred embodiment of the invention, referred particularly to the drawings, which form an integral part hereof.

BRIEF DESCRIPTION OF THE DRAWINGS

FIG. 3 is a view along line a–a' of FIG. 2, where the variations in density along the core are perfectly shown.

DETAILED DESCRIPTION OF THE INVENTION

Figure 1:
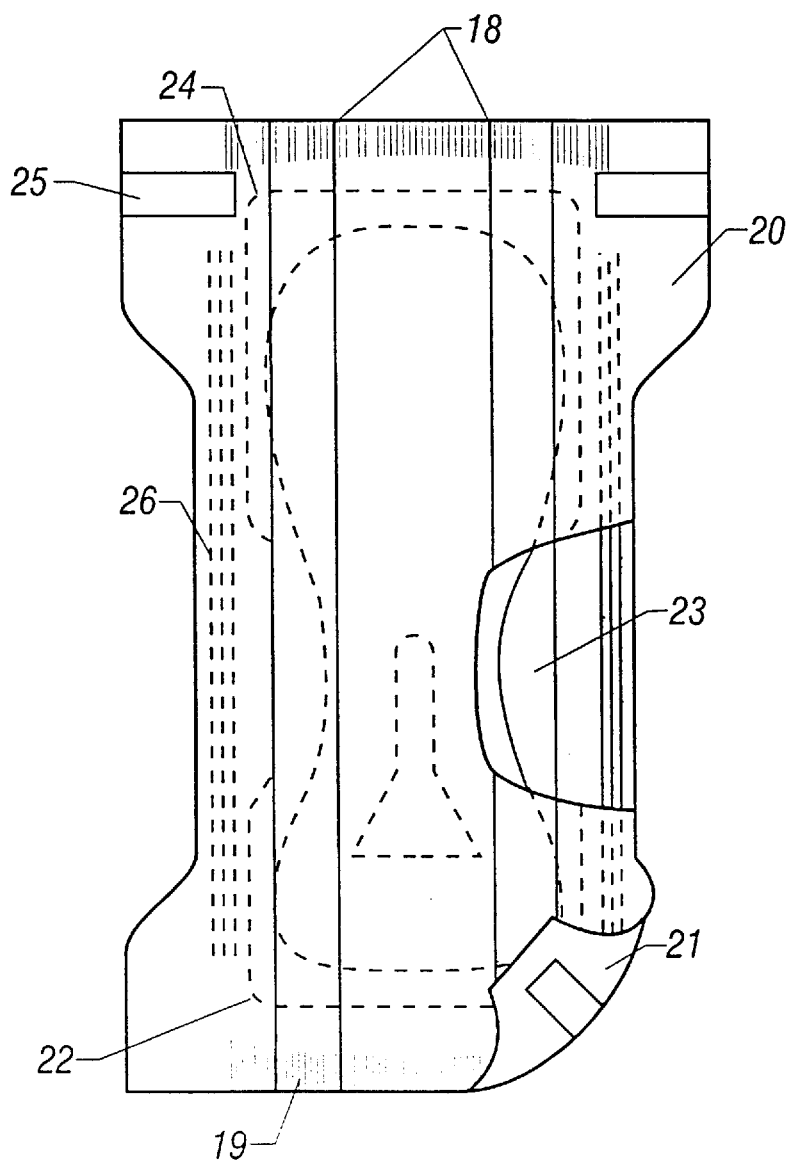
FIG. 1 shows a diaper with all its components, having a part cut so the details of construction are shown; in the absorbent core the reception, distribution-storage, and anti-leakage zones can be seen.

FIG. 1 shows a diaper with all its components. It is formed by a topsheet (20), a backsheet (21), and an absorbent core

(22) that is placed between the topsheet and the backsheet, a fastening system (25), crotch elastic (26), two open adjustment members (18), and a waist elastic (19). The diaper may or may not have a distribution material layer (23) that may wrap wholly the absorbent core, be placed all along in the central part of it by both sides of the core, or cover only the central part of it by the upper or the lower part.

The topsheet and the backsheet have the same dimensions and are longer and wider than the absorbent core. The part that projects out of the absorbent core (24) forms the outline of the diaper and the cut that is made upon this outline will be the final shape of the diaper. In the figure an "I" shape is shown, but it can have any other proper or desired shape.

The topsheet (20) is pervious to fluids, must be soft and must not irritate the user's skin, generally non woven polyester, rayon, polypropylene, polyethylene fabric or mixtures of these is used.

The backsheet (21) is impervious to fluids, must be soft and must resist the user's movements. Generally low density polyethylene is used, although any material of the described characteristics may be used.

The fastening system (25) may be constituted by three bands, two adhesive bands and a front band, which are one protective and one or two adhesive or by any other fixing means for the diaper.

The crotch elastic elements (26) may be constituted by one or many threads or filaments, that are joined to the inner part of the diaper's backsheet by means of an adhesive. These filaments, when fixed to the backsheet, are stressed so that when stress is removed they retract and provide the function of an elastic. To achieve the adjustment in the user's waist, in a preferred embodiment of the invention a polyurethane foam band is used, that is fixed by means of an adhesive to the topsheet and the backsheet of the diaper. Upon fixing, the band is stressed, so that when stress disappears it provides the function of an elastic and the adjustment in the waist is achieved upon placing the diaper.

The open adjustment members (18) are two parallel bands that are placed along the whole diaper and have elastic in one of its terminals so that they adjust to the user and form a first retaining barrier of the liquid and solid exudates discharged from the body of the user. The material for these adjustment members is liquid impervious non woven fabric, as it is well known in the art.

The absorbent core (22) is formed by fibers of an absorbent material (27), generally cellulose, mixed with particles of superabsorbent material (28). As absorbent material, fiber-depleted cellulose may be used, either in its natural state or mixed with various components, and as superabsorbent material water insoluble polymers with acidic terminations may be used.

The technical principles upon which the present invention is based are:

A) The pulp fibers, of which the absorbent material is constituted, work by means of capillarity, this is, the liquid does not introduce through them, but these being in contact with the liquid, they cause it to distribute flowing through them and remaining stored in them.

B) The superabsorbent material, on the other hand, captures the liquid, introducing inside each of the particles of it until every one of them is saturated. These particles, once saturated, are resistant to explosion when put under pressure, this is, the liquid will stay trapped inside them.

C) While density increases inside the absorbent core, the liquid distribution will be faster in one plane only because of the reduction of space between the fibers of pulp, that is, the increase in the capillarity forces. Simultaneously by the same reason, the liquids are trapped slowly.

D) While density decreases there is a quicker absorption, because there is more space for the capture of liquids.

E) At lower densities in the absorbent core, the liquid distribution will be slower because of the reasons exposed in C; however, a distribution in all dimensions will be achieved because the liquid will be able to flow more freely.

F) Once the liquid is distributed in the high density zones, it remains completely trapped between the fibers and in this way it avoids returning to the surface of the core; this is why the high density zone is better for storing the fluids.

G) The liquids always flow from the low density zones to the high density zones, and never in the opposite way. This means that the fluid flow is eased from zones with higher capillary radius to zones with lower capillary radius and it is hindered or stopped in the opposite way.

H) The superabsorbent material, if not distributed correctly, may cause blocking and diminish the liquid distribution; because of it, it must be placed in the zone where it is most needed and mixed with the absorbent material to avoid the blocking.

All the foregoing is supported mathematically by the Lucas and Laplace equations, that establish:

$$dh/dt = r\gamma \cos\Theta / 4\eta h \qquad \text{Lucas equation}$$

$$p = 2\gamma \cos\Theta / r \qquad \text{Laplace equation}$$

where:

r=capillary radius $\gamma$=liquid surface tension $\Theta$=contact angle $\eta$=liquid viscosity h=liquid height in the capillary p=pressure or force with which the liquid is sustained in the capillaries From the Lucas equation it is deducted that the velocity in the fluid movement through the capillaries is determined by the size of these, which indicates that in big empty spaces, obtained in low densities (reception zone), the liquid absorption is fast, it has little fluid retention and allows the transfer of these to high density zones.

From the Laplace equation it is established that the force with which the fluids are "tied" in the capillaries is higher as the radius of the capillary is smaller. It has been proved that high density cores have lower liquid returns (distribution-storage zone).

Considering the foregoing, the reception zone must have a much lower density than the distribution-storage zone to receive the liquid and distribute it in all directions to that zone. And the anti-leakage zone must have lower density than the distribution-storage zone to avoid the liquid flowing to it and in that way it may remain dry.

The density considered right for the reception zone is of about 0.015 to 0.09 $g/cm^3$; for the distribution-storage zone is of about 0.1 to 0.3 $g/cm^3$ and for the anti-leakage zone is of about 0.04 to 0.1 $g/cm^3$.

Figure 2:
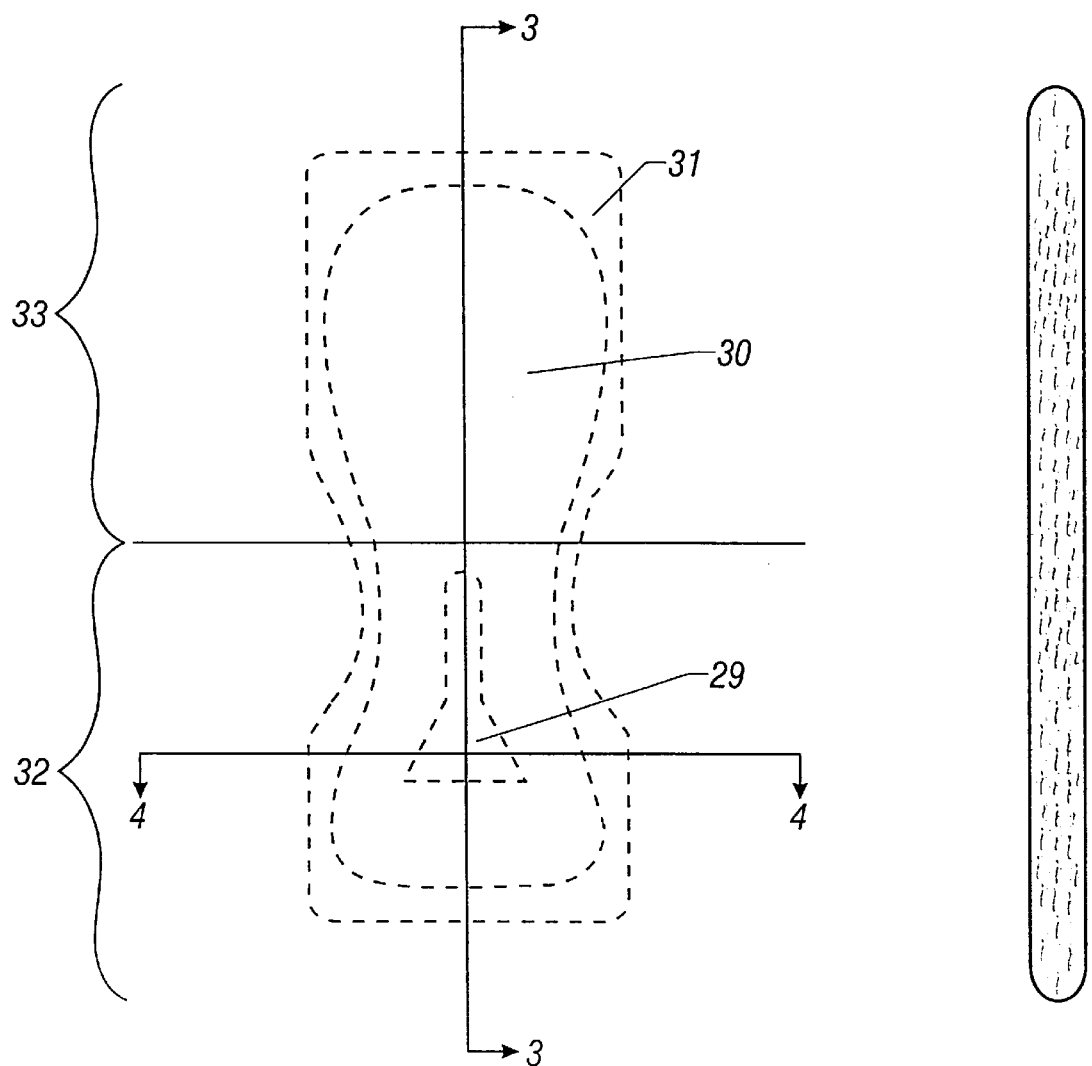
FIG. 2 is a plan view of the absorbent core, where the three zones can be clearly appreciated.

FIG. 2 shows a drawing of the absorbent core, in which the three zones formed by distributing the absorbent core's material in such way that it works more efficiently can be seen: the reception zone (29), the distribution-storage zone (30), and the anti-leakage zone (31).

The absorbent core is divided in FIG. 2 in two sections by means of line 34: the front section (32), that includes around 50% of the absorbent core, and the back section (33), that includes the remaining 50% of the absorbent core.

The reception zone (29) has the shape of a long-neck flask and includes an area that is from 5 to 20% of the core's front section. Its density, considering the absorbent material already mixed with the superabsorbent material, is of about 0.015 to 0.09 g/cm$^3$ and preferably is of about 0.05 to 0.07 g/cm$^3$.

The correct shape of the reception zone was determined after several tests with boys and girls of different weights and ages. It was waited until the user wetted the diaper for the first time and at that time it was determined the exact area in which the urine dropped. The conclusion was that both, boys and girls, wet first the diaper's front section but in different zones. The boys use the zone that has the triangle shape in FIG. 2 and girls use the flask's neck and the upper apex of the triangle. With the obtained results in this experiment it was determined also the right area for the reception zone.

The distribution-storage zone (30) surrounds wholly the reception zone and includes an area that is around 45% to 75% of the absorbent core's total area.

Its density varies in the range of about 0.1 to 0.3 g/cm$^3$, preferably between about 0.14 to 0.18 g/cm$^3$.

The anti-leakage zone (31) includes an area that is of about 20 to 50% of the absorbent core's total area and shapes the whole outline of it, has a density lower than the distribution-storage zone so that it creates a change in the capillary size, making them bigger; so that the flow stops or becomes difficult from the distribution-storage zone to the anti-leakage zone, and therefore prevent the liquid from going out of the absorbent core. The density of this zone is of about 0.04 to 0.1 g/cm$^3$, and preferably of about 0.065 to 0.075 g/cm$^3$.

Figure 5:
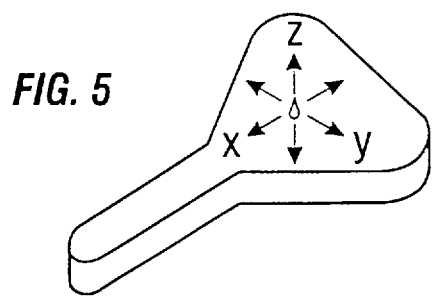

According to the technical principles exposed, liquid will fall in the reception zone and immediately be absorbed and distributed in all directions (X, Y, Z) to the distribution-storage zone, which may be seen clearly in FIG. 5. The density difference between both zones will help the liquid flow to be fast from the reception zone to the distribution-storage zone, because the fluids move easily from capillaries with big radius to the ones with smaller radius. Having the distribution-storage zone a high density, the capillarity forces will rise and the liquid will flow rapidly in only one plane towards every place in this zone. Being this zone more dense than the reception zone, besides producing speed in the fluid flow, it will retain or tie fluid, so that a low return of liquids to the surface is assured.

Figure 4:
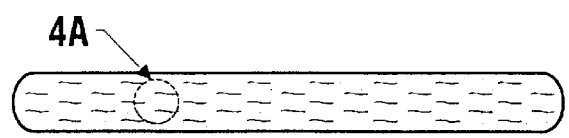
FIG. 4 shows a view along the line B–B' of FIG. 2, where the differences in density of the three zones as well as how the superabsorbent material is uniformly distributed in these zones can be observed.
Figure 4A:
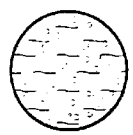

The superabsorbent material (28), which can be clearly observed in FIGS. 3 and 4, is distributed preferably homogeneously along the whole core. In this way, it helps supporting the structure of the core when the diaper is wet and keep the baby dry at any moment.

One may think that according to the little specific gravity of the reception zone, it may be convenient that there are no particles of superabsorbent material to avoid blocking, but it is important that there is in a minimum amount, because when the liquid falls these particles will inflate avoiding that the absorbent material fibers (cellulose) compress and make an empty space in this zone. On the other hand, by inflating the superabsorbent material particles spaces will be made so that if the user urinates again on the same diaper, the reception zone will continue developing its function. This will occur also in the distribution-storage zone and instead of causing blocking, the superabsorbent material will help the liquid distribute better. It is also very important the presence of superabsorbent material in this zone, because it will help absorption and liquid retention. The fiber/superabsorbent material relation varies in a ratio of about 60/40 to 95/5.

The absorbent core may be made in many shapes and sizes. In the figures, a hourglass shape is shown but this may vary according to the manufacturing method.

In FIG. 3 the differences in thickness and density along the whole diaper and in the different zones may be seen clearly. The distribution-storage zone is the one with greater density, followed by the anti-leakage zone, and at last the reception zone.

We claim:

1. A disposable diaper comprising:
   a fluid pervious topsheet;
   a fluid impervious backsheet; and
   an absorbent core, placed between the topsheet and the backsheet, that includes three zones, each consisting of an absorbent material mixed with particles of superabsorbent material, including:
      a fluid reception zone positioned to receive fluid discharged by a wearer;
      a primary storage zone encircling the fluid reception zone to store the fluid received by the fluid reception zone; and
      an anti-leakage zone encircling the primary storage zone and having a lower density than the primary storage zone to deter the fluid from leaving the primary storage zone.

2. The disposable diaper of claim 1, wherein the fluid reception zone, the primary storage zone, and the anti-leakage zone each have different densities.

3. The disposable diaper of claim 1, wherein the absorbent core has a front half and a rear half and the fluid reception zone comprises from about 5% to about 20% of the surface area of the front half.

4. The disposable diaper of claim 1, wherein the fluid reception zone has a long-neck flask shape.

5. The disposable diaper of claim 1, wherein the fluid reception zone has a density in a range of about 0.015 g/cm$^3$ to about 0.09 g/cm$^3$.

6. The disposable diaper of claim 1, wherein the fluid reception zone has a density in a range of about 0.05 g/cm$^3$ to about 0.07 g/cm$^3$.

7. The disposable diaper of claim 1, wherein the primary storage zone entirely encircles the fluid reception zone in a given cross-section.

8. The disposable diaper of claim 1, wherein the primary storage zone comprises about 45% to about 75% of the surface area of the absorbent core.

9. The disposable diaper of claim 1, wherein the primary storage zone has a density in a range of about 0.1 g/cm$^3$ to about 0.3 g/cm$^3$.

10. The disposable diaper of claim 1, wherein the primary storage zone has a density in a range of about 0.14 g/cm$^3$ to about 0.18 g/cm$^3$.

11. The disposable diaper of claim 1, wherein the anti-leakage zone entirely encircles the primary storage zone in a given cross-section.

12. The disposable diaper of the claim 1, wherein the anti-leakage zone comprises about 30% to about 50% of the surface area of the absorbent core.

13. The disposable diaper of claim 1, wherein the anti-leakage zone has a density in a range of about 0.04 g/cm$^3$ to about 0.10 g/cm$^3$.

14. The disposable diaper of claim 1, wherein the anti-leakage zone has a density in a range of about 0.065 g/cm$^3$ to about 0.075 g/cm$^3$.

15. The disposable diaper of claim 1, wherein the ratio of absorbent material to superabsorbent material in the absorbent core is in a range of about 95/5 to about 60/40.

16. The disposable diaper of claim 1, wherein the superabsorbent material is mixed homogeneously with the absorbent material in each of the three zones of the absorbent core.

17. A disposable diaper comprising:

a fluid pervious topsheet;

a fluid impervious backsheet; and an absorbent core, placed between the topsheet and the backsheet, that includes three zones, each consisting of an absorbent material mixed with particles of a superabsorbent material, including:

a fluid reception zone positioned primarily in a front half of the absorbent core to receive fluid discharged by a wearer and having a density in a range of about 0.015 g/cm$^3$ to about 0.09 g/cm$^3$;

a primary storage zone encircling the fluid reception zone, comprising about 50% to about 80% of the surface area of a rear half of the absorbent core, and having a density in a range of about 0.1 g/cm$^3$ to about 0.3 g/cm$^3$, to store the fluid received by the fluid reception zone; and an anti-leakage zone encircling the primary storage zone and having a density in a range from about 0.04 g/cm$^3$ to about 0.1 g/cm$^3$, to deter the fluid from leaving the primary storage zone.

18. The disposable diaper of claim 17, wherein about 60% to 90% of the superabsorbent material is located in the primary storage zone of the absorbent core and the rest of the superabsorbent material is mixed homogeneously throughout the absorbent core.

* * * * *